US011361603B1

(12) United States Patent
Ismail

(10) Patent No.: US 11,361,603 B1
(45) Date of Patent: Jun. 14, 2022

(54) METHOD AND APPARATUS FOR SECURE DELIVERY OF TAKE-OUT FOOD

(71) Applicant: Mohammad Ismail, Fulshear, TX (US)

(72) Inventor: Mohammad Ismail, Fulshear, TX (US)

( * ) Notice: Subject to any disclaimer, the term of this patent is extended or adjusted under 35 U.S.C. 154(b) by 0 days.

(21) Appl. No.: 17/498,735

(22) Filed: Oct. 11, 2021

Related U.S. Application Data

(60) Provisional application No. 63/090,292, filed on Oct. 12, 2020.

(51) Int. Cl.
| | |
|---|---|
| *G07C 9/00* | (2020.01) |
| *B65D 55/02* | (2006.01) |
| *B65D 33/02* | (2006.01) |
| *B65D 33/25* | (2006.01) |
| *A47J 47/14* | (2006.01) |
| *G06Q 10/08* | (2012.01) |
| *A61L 2/10* | (2006.01) |
| *B65D 1/22* | (2006.01) |
| *B65D 50/00* | (2006.01) |
| *B65D 55/14* | (2006.01) |
| *E05B 65/52* | (2006.01) |

(52) U.S. Cl.
CPC .......... *G07C 9/00571* (2013.01); *A47J 47/14* (2013.01); *A61L 2/10* (2013.01); *B65D 1/22* (2013.01); *B65D 33/02* (2013.01); *B65D 33/2566* (2013.01); *B65D 50/00* (2013.01); *B65D 55/02* (2013.01); *B65D 55/14* (2013.01); *G06Q 10/0832* (2013.01); *A61L 2202/11* (2013.01); *A61L 2202/14* (2013.01); *A61L 2202/23* (2013.01); *E05B 65/5276* (2013.01)

(58) Field of Classification Search
CPC .... B65D 50/02; B65D 50/00; B65D 2555/02; B65D 1/22; B65D 33/02; B65D 33/2566; B65D 55/02; B65D 55/14; G07C 9/00571; A47J 47/14; A61L 2/10; A61L 2202/11; A61L 2202/14; A61L 2202/23; G06Q 10/0832; E05B 65/5276
See application file for complete search history.

(56) References Cited

U.S. PATENT DOCUMENTS

| | | | | | |
|---|---|---|---|---|---|
| 1,148,773 | A | * | 8/1915 | Helmers | E05B 47/0012 109/43 |
| 3,893,096 | A | * | 7/1975 | Tucci | G08B 13/149 340/571 |
| 4,118,692 | A | * | 10/1978 | Fitchett | A45C 13/24 109/43 |
| 4,426,862 | A | * | 1/1984 | Yamada | E05B 47/0002 70/278.1 |
| 4,522,047 | A | * | 6/1985 | Johl | H02J 7/35 70/19 |
| 5,153,561 | A | * | 10/1992 | Johnson | A45C 13/24 190/101 |
| 5,235,822 | A | * | 8/1993 | Leonovich, Jr. | A45C 11/20 455/344 |

(Continued)

*Primary Examiner* — Kareen K Thomas
(74) *Attorney, Agent, or Firm* — Karen B. Tripp

(57) ABSTRACT

A secure food delivery bag with a single point for securing closure with a lock having an associated QR code or pin code enabled access control. The QR code or pin code is uniquely set for each use of the bag and is provided to the intended recipient of the food at the time the food is placed and locked in the bag. The recipient uses the unique QR code or pin code to access the bag contents upon receipt of the bag.

18 Claims, 7 Drawing Sheets

(56) References Cited

U.S. PATENT DOCUMENTS

| | | | | |
|---|---|---|---|---|
| 5,447,041 | A * | 9/1995 | Piechota | A45C 15/00 |
| | | | | 312/405.1 |
| 5,781,853 | A * | 7/1998 | Johnson | A45C 15/00 |
| | | | | 455/350 |
| 6,305,185 | B1 * | 10/2001 | Sloan | A45C 5/14 |
| | | | | 62/235.1 |
| 10,635,956 | B2 * | 4/2020 | Mann | G06K 19/06037 |
| 11,091,872 | B1 * | 8/2021 | Somaya | D06F 95/006 |
| 2020/0051015 | A1 * | 2/2020 | Davis | G06Q 50/28 |
| 2020/0165861 | A1 * | 5/2020 | Bruno | B65D 81/38 |
| 2021/0289903 | A1 * | 9/2021 | Parker | A45C 11/20 |

\* cited by examiner

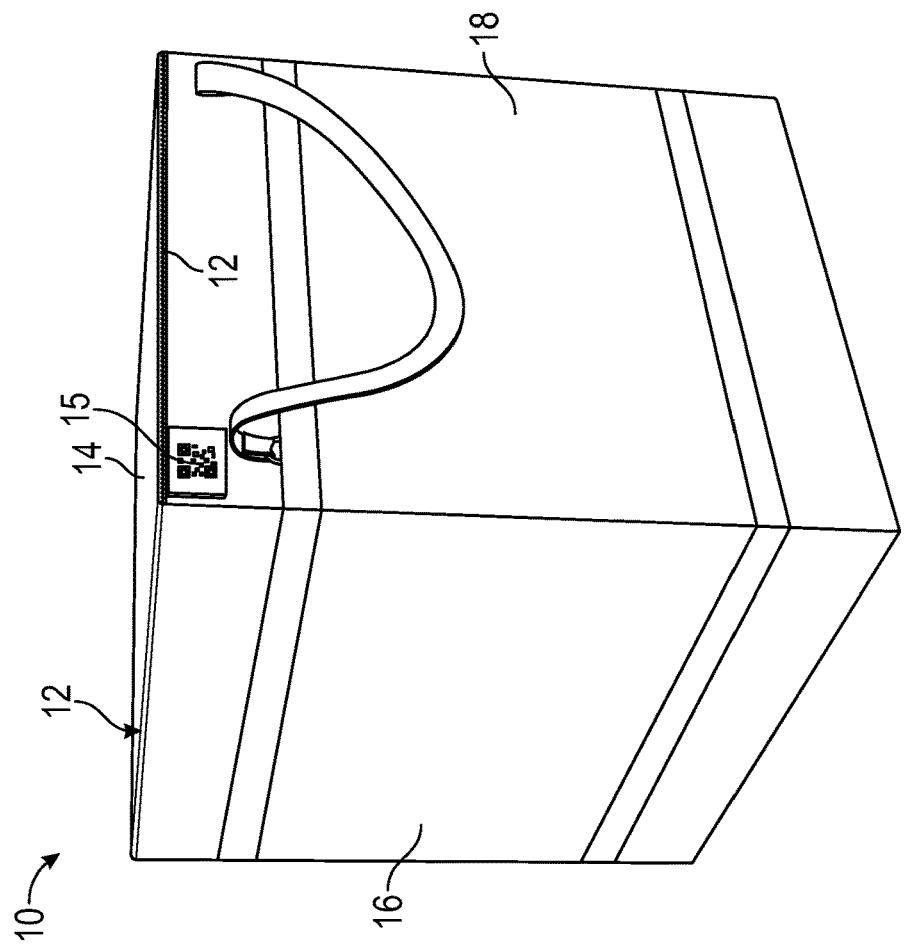
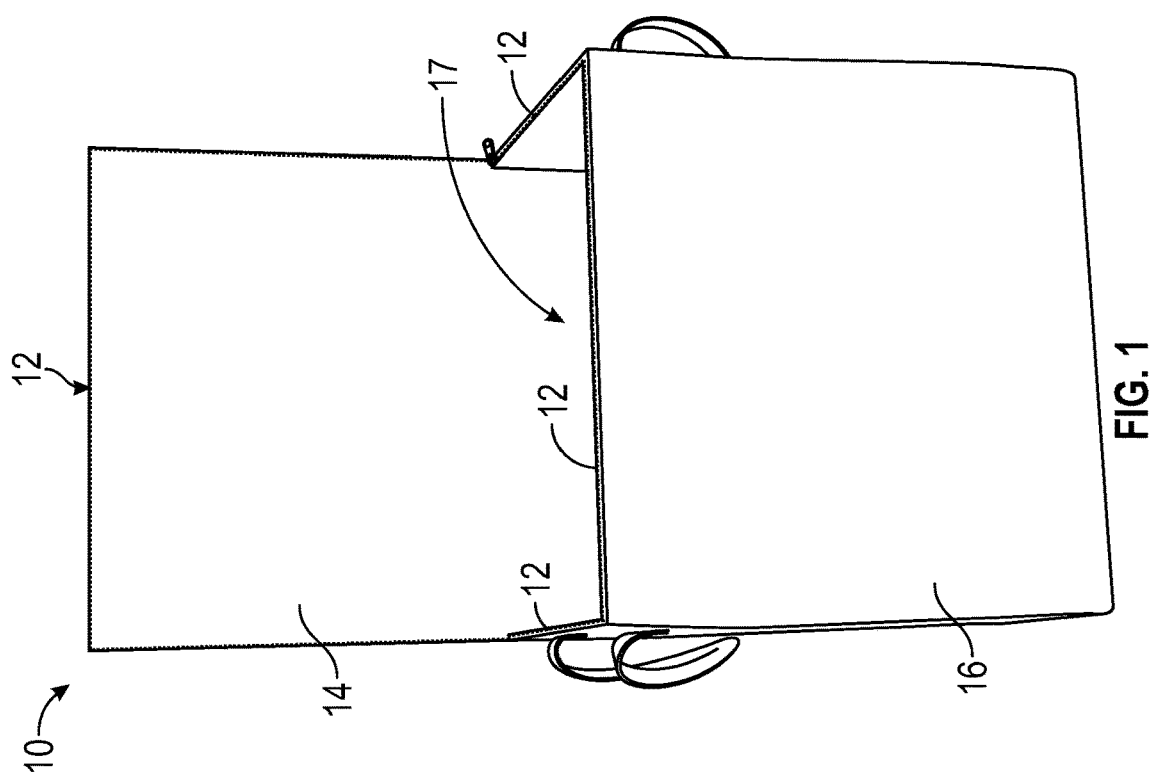

METHOD AND APPARATUS FOR SECURE DELIVERY OF TAKE-OUT FOOD

CROSS REFERENCE TO RELATED APPLICATION

The invention claims priority from U.S. Provisional Patent Application No. 63/090,292, filed Oct. 12, 2020.

FIELD

The present invention relates to bags and containers for take-out food or other food for delivery from restaurants, grocery stores, and food shops to consumers in their homes and workplaces. More particularly, the present invention relates to methods and apparatuses for securing the delivery of such food without tampering en route.

BACKGROUND

Take-out and delivery food from restaurants, grocery stores and other food shops is a growing trend in the food industry, and the deliveries are increasingly being made by various third party delivery services, as well as by the employees and contractors of the restaurants, stores, and shops. Social media commonly reflects experiences of consumers who receive their delivered food showing evidence of tampering, apparently by the delivery drivers or other unknown persons.

To address this situation and reassure consumers of the integrity of their food packaging, restaurants, grocery stores, and food shops have increasingly begun to use tamper-evidence bags. Even when such bags indicate evidence of tampering, however, they do not otherwise particularly hinder the tampering.

A need exists for better securing food in packaging for delivery to customers.

SUMMARY

The present invention provides a secure food delivery bag that deters tampering, or at least makes tampering more difficult to accomplish. The bag of the invention has a means for closure at essentially a single point or location so that an electromechanical lock can secure the closure at that point or location. The lock fastens over that single point for securing the closure when the lock is activated or closed in position. The lock releases and allows access to the closure for opening the bag when the lock is deactivated or opened The lock is associated with a QR code or pin code enabled access control, and activation and deactivation of the lock is controlled or effected by entering the QR code or pin code associated with the lock into the access keypad. A QR code or pin code is temporary and uniquely set for each use of the bag.

In use, the food supplier receives an order for food from the intended recipient of the order, places the ordered food in the secure delivery bag of the invention, and sets the lock with a unique QR code or pin code, fastening the bag closed with the lock and unique QR code or pin code. At about that same time as setting the lock, the food supplier sends the unique QR code or pin code for opening the lock to the intended recipient via cellular data or the internet, or otherwise through the internet of things, and the intended recipient receives the unique QR code or pin code. The food supplier then gives the secure delivery bag containing the food to a deliverer of the food. The deliverer of the food delivers the secure delivery bag to the intended recipient. The intended recipient opens (or has opened on their behalf) the secure delivery bag with the unique QR code or pin code for the secure delivery bag and takes the food from the bag.

BRIEF DESCRIPTION OF THE DRAWINGS

The present invention will be better understood by referring to the following detailed description of preferred embodiments and the drawings referenced therein, in which:

FIG. 1 is a front perspective view of one embodiment of the secure delivery bag of the present invention showing the top of the bag unzipped and open for receiving food for delivery in the bag.

FIG. 2 is a side perspective view of the bag of FIG. 1, showing one embodiment of the lock of the invention that secures closure of the bag for secure delivery.

LIST OF ELEMENTS IN DRAWINGS

10 One embodiment of a secure delivery bag of the invention, shown in Figures and 2.
12 Zipper.
14 Top of the bag of FIGS. 1 and 2.
16 Front side of the bag of FIGS. 1 and 2.
18 Side of the bag of FIGS. 1 and 2 showing one embodiment of lock of the invention.
20 Another embodiment of a secure delivery bag of the invention, shown in FIGS. 3, 4, 5, and 6.
22 Pair of zipper pulls for zipper closure of bag in FIGS. 3, 4, 5, and 6.
24 Top of the bag of FIGS. 3, 4, 5, and 6.
25 Frame of lock of bag in FIGS. 3, 4, 5, and 6.
26 Front of the bag of FIGS. 3, 4, 5, and 6.
28 Side of the bag of FIGS. 3, 4, 5, and 6 showing another embodiment of a lock of the invention.
30 Door of lock of bag in FIGS. 3, 4, 5, and 6.
32 Hinge of door of lock of bag in FIGS. 3, 4, 5, and 6.

Figure 5:
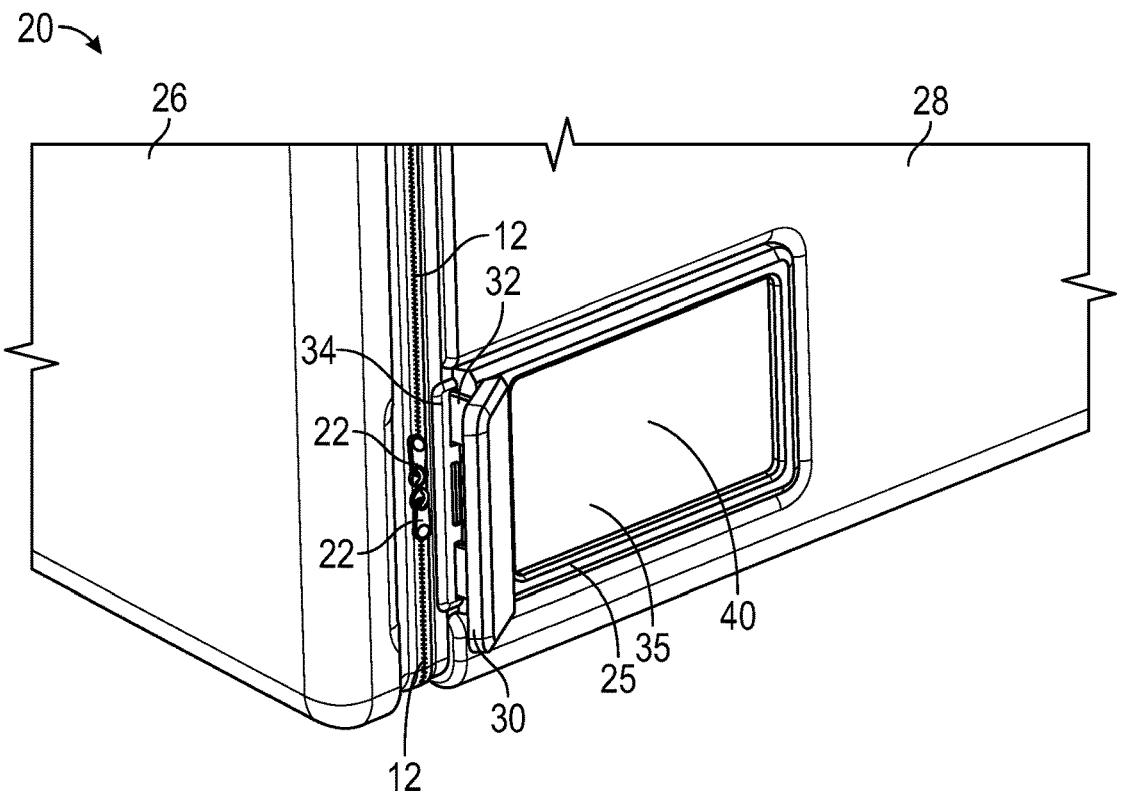
FIG. 5 is close-up, front perspective view of the lock of the bag in FIGS. 3 and 4, showing the lock partially open and revealing the underlying two zipper pulls that close the zipper closure of the bag and that were secured under the lock when the lock was closed as in FIG. 4.
Figure 6:
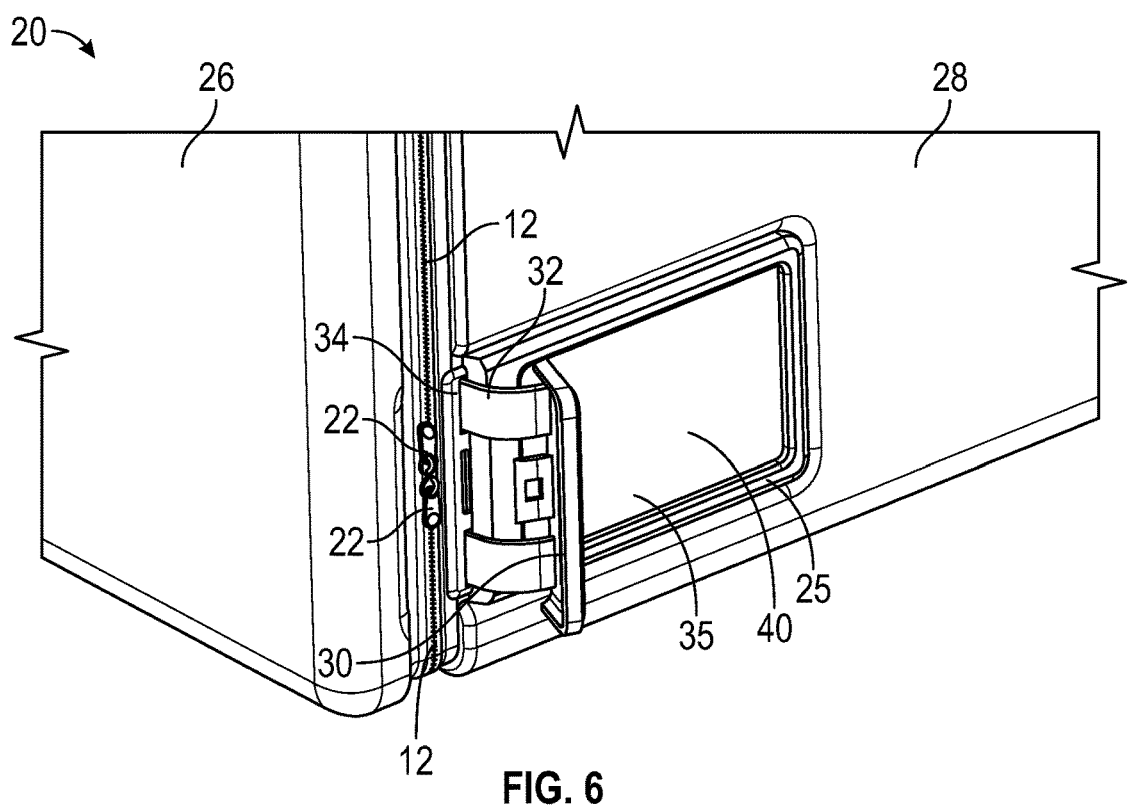
FIG. 6 is another close-up, front perspective view of the lock of the bag in FIGS. 3, 4, and 5, showing the lock fully open.
Figure 7:
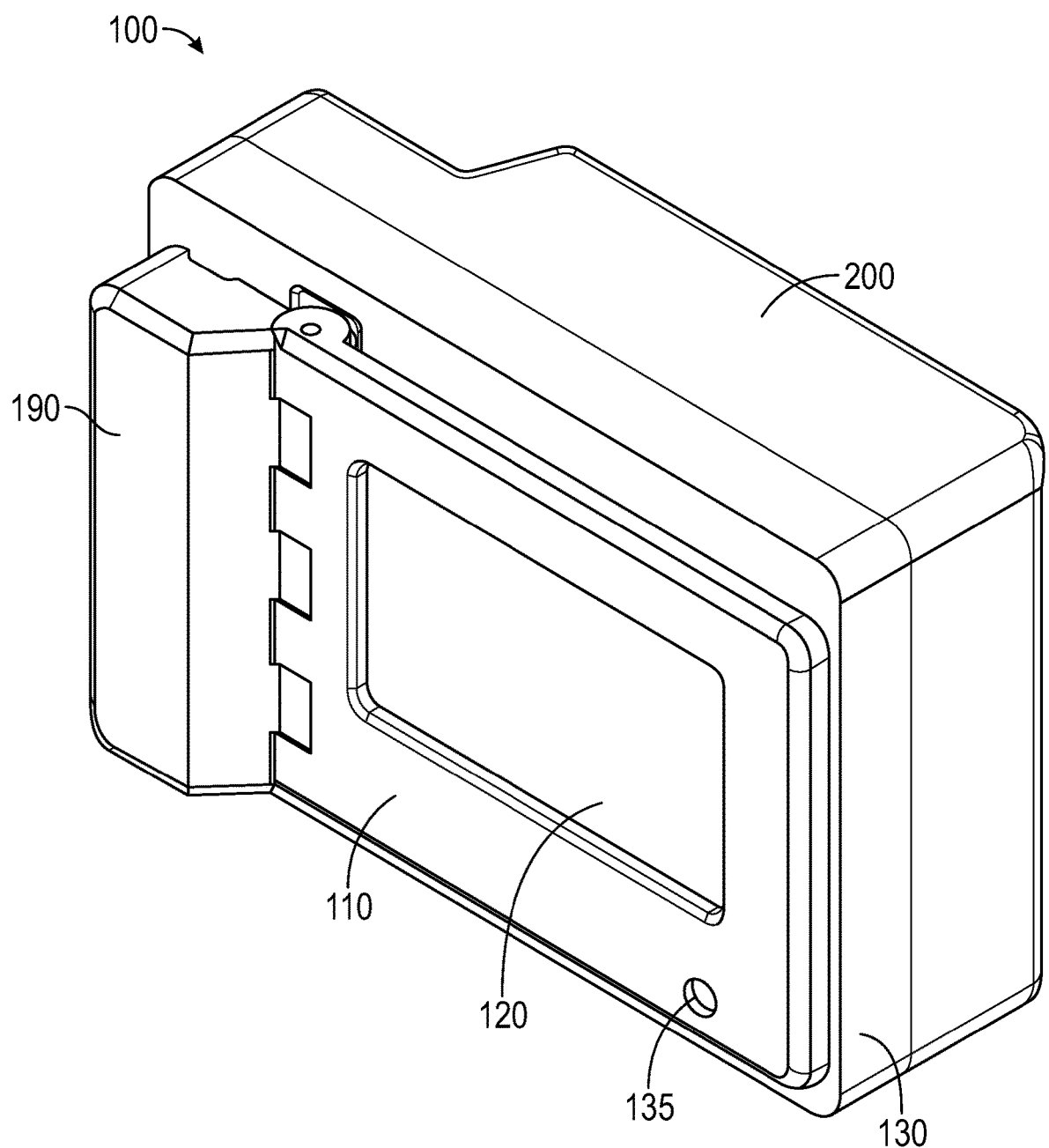
FIG. 7 is a front perspective view of still another embodiment of the lock of the invention, such as could be used in the bags shown in FIGS. 1 and 3, or other embodiments of the bag of the invention.

35 Access control screen of lock of bag in FIGS. 3, 4, 5, and 6.
34 34 Portion of lock of bag in FIGS. 3, 4, 5, and 6 that supports hinge 32.
40 Alternative embodiment of lock of the invention shown on bag of the embodiment of the invention in FIGS. 3, 4, 5, and 6.
100 Another alternative lock of the invention.
110 Front case of the lock of the invention shown in FIG. 7.
120 Screen of the lock of the invention shown in FIG. 7.
130 Middle section of case of the lock of the invention shown in FIG. 7.
135 Port for battery charger
140 GPS
150 Pin
160 Latch
170 Spring
180 Second Spring
190 Door of lock of the invention shown in FIG. 7
200 Back of lock of the invention shown in FIG. 7
210 PI Board
220 Solenoid (associated with operation of latch of lock)
230 Makerbot Limit Switch Board
240 Battery
250 LED Board
260 Back section of case of the lock of the invention shown in FIG. 7
270 Interior of bag of the invention showing lock of invention installed in the bag and ultraviolet LED lights at back of lock available for projecting ultraviolet light into interior of bag.

DETAILED DESCRIPTION

The present invention provides a bag for delivery of food that allows the food contents of the bag to be secured from tampering en route between the source of the food, such as a restaurant, grocery store, or food shop, for example, and the intended recipient, such as the orderer and intended consumer of the food, for example. The security is provided primarily through an electromechanical lock securing closure of the bag, which is opened and closed using a QR code, or pin, access control technology, or in a broader or more general sense, employing simple IoT technology, as will be discussed in more detail below.

Any number of various shaped bags can be used in the invention-either horizontal configurations or vertical configurations, in three dimensional form or in two dimensional form, as desired to optimize use depending on the type of food to be transported. For example, a horizontal configuration may accommodate individual boxed pizzas or platters or large flat items, while a vertical configuration may accommodate multiple pre-made meals and other food, including beverages such as wine bottles. As used herein, the term "food" is intended to include "beverages" unless otherwise noted.

In some embodiments, the bag may be a soft-sided container. In some other embodiments, the bag may be comprised of rigid or semi-rigid materials. In one embodiment, the bag of the invention will have six panels forming a rectangular (or square) shape with four of the six panels serving as sides and one as a top and one as a bottom. In one embodiment, the bag can comprise a rigid frame, and in another embodiment at least some panels that form the sides of the bag may include rigid features, to maintain a shape of the bag to have a formed, internal cavity for receiving food (which may also be individually packaged in containers).

For example, the bag may be formed of a hard or soft plastic, a light-weight metal, or a woven or non-woven fabric or fabric-like material, such as a multi-layer polypropylene or a polyurethane laminate. For another example the bag may be formed primarily of nylon fabric or other materials that resist wear, resist stains, and resist smell.

However, for effectiveness in the invention, the bag of the invention should be comprised of a material that resists tearing and is difficult to puncture. The bag of the invention should also have only one opening, and that opening should be closeable with a closure that can be controlled at one point or location. In preferred embodiments, the bag of the invention is opened and closed with a zipper or multiple zippers that begin at the same point or location.

For example, referring to the embodiment of the invention shown in FIGS. 1 and 2, bag 10 has a relatively soft-sided but rigid frame, box-type structure with a top 14 that closes on three sides of that top, connecting it to the front 16 and sides 18 of the bag, with a zipper 12. The zipper begins to open and completes closure at the lock 15. Lock 15 of the bag opens with a specific QR code input by the food provider. Lock 14 has a projectile that interferes with movement of the zipper and the beginning of the zipper, or the zipper pull, is immediately in front of the projectile when the zipper is closed so that the projectile prevents opening of the zipper. Such projectile (not specifically shown in the Figures), can underlie the top surface of the bag 10 so that it is not easily damaged when the bag is in use or being transported.

FIGS. 3, 4, 5, and 6 show a relatively hard-sided secure delivery bag of the invention 20 with an alternative lock 40. Lock 40 is positioned on the bag at the point or location that zippers 12 have a pair of zipper pulls 22 for opening and closing the bag, such that when door 30 of lock 40 is closed, the door 30 closes over the zipper pulls 22 preventing operation of the zipper 12 and preventing opening of the bag 20. In this embodiment, lock 40 is opened with a pin code, set by the originator—the food provider, for example—and given to the intended recipient of the contents of the bag through cellular data.

Figure 3:
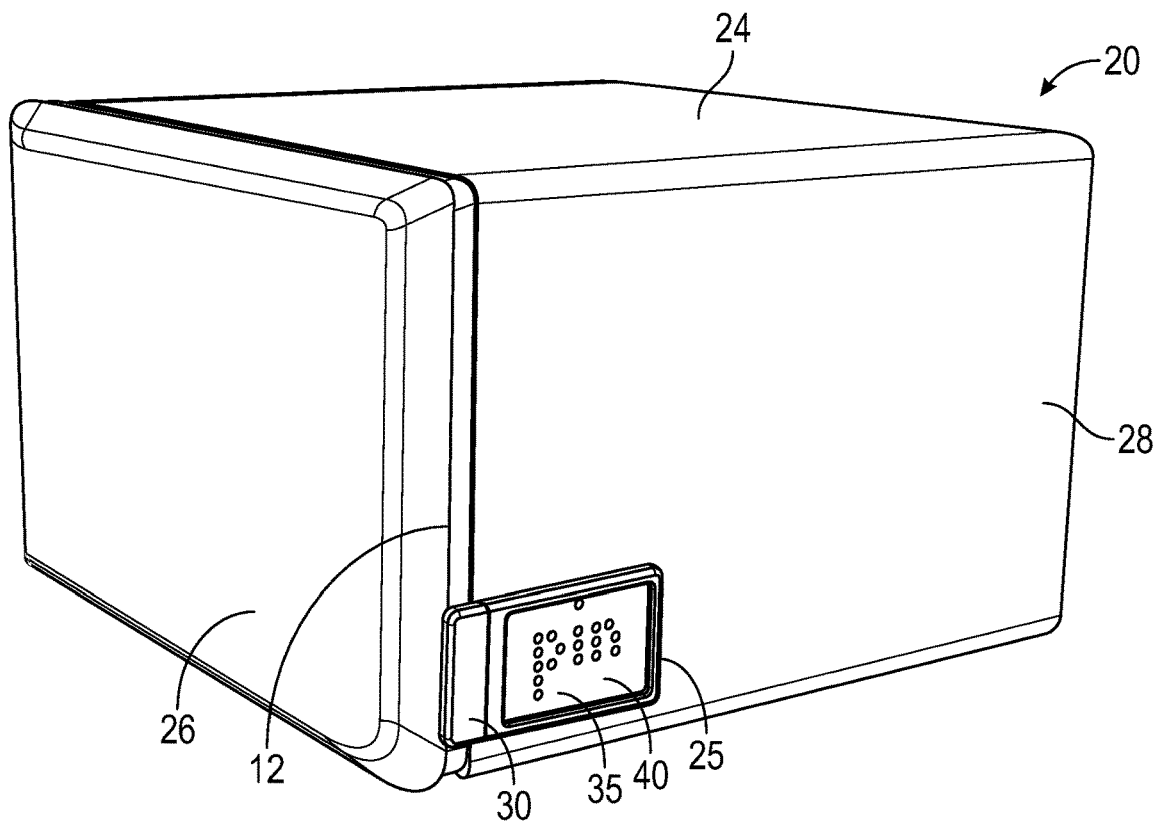
FIG. 3 is a side perspective view of another embodiment of the secure delivery bag of the present invention, showing another embodiment of the lock of the invention that secures closure of the bag for secure delivery.
Figure 4:
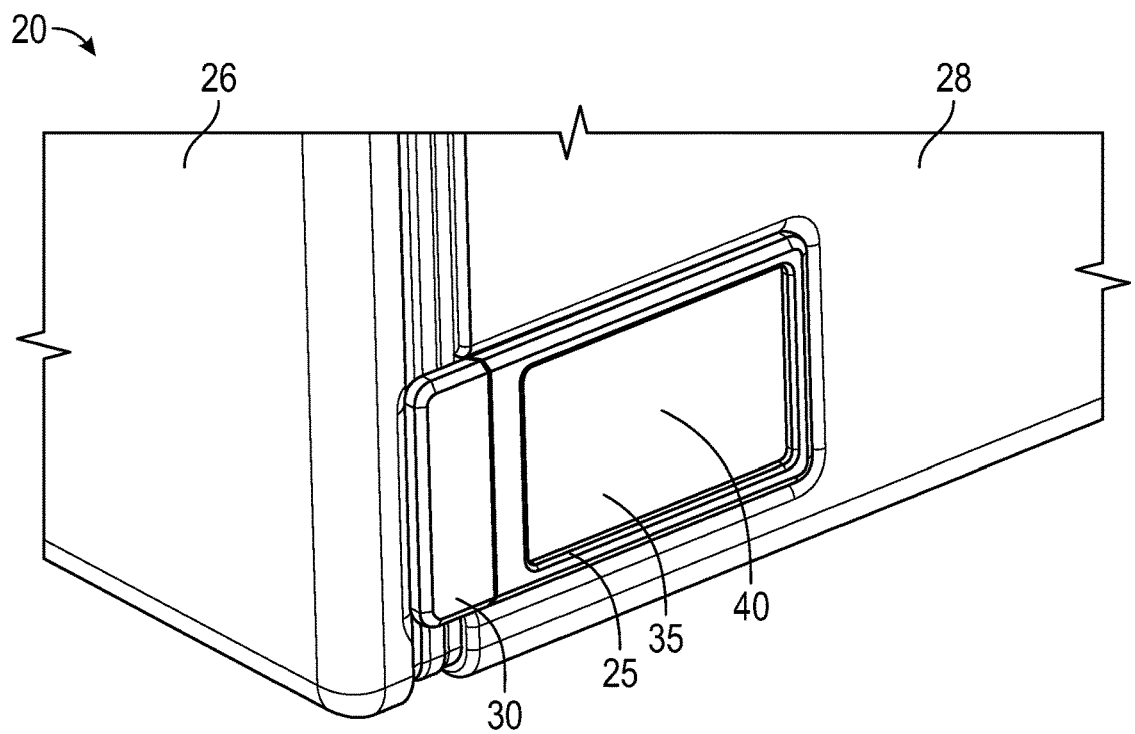
FIG. 4 is a close-up, front perspective view of the lock of the bag in FIG. 3 showing the lock in the closed position, securing closure of the bag.
Figure 8:
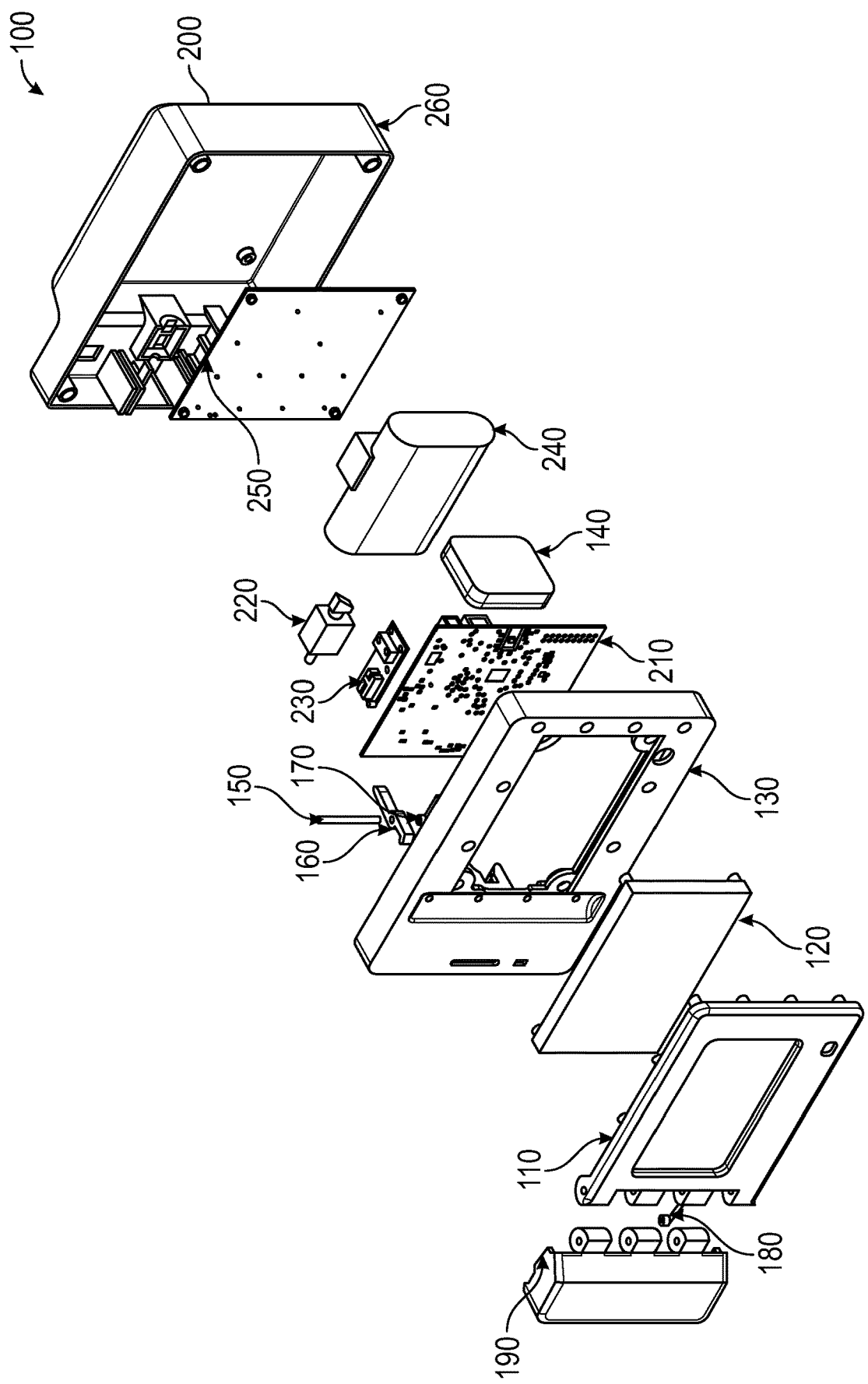
FIG. 8 is a blown-apart view of the lock shown in FIG. 7.

FIGS. 7 and 8 show another embodiment of the lock of the invention, which can be used on either embodiment of the bag of the invention shown in FIGS. 1 and 3 and in many other variations of such delivery bags of the invention for delivering food in a secure manner. Variations of door 190 on this lock 100, substantially like door 30 on lock 40, positions over the point or location of the opening of the bag so that when the lock is engaged, or closed, the mechanism for opening the bag cannot be used to open the bag. When the bag is closed with a zipper, such location of the door of the lock can be immediately behind the zipper pull when the bag is closed with the zipper in an alternative embodiment to the door of the lock being immediately over the zipper pull of the zipper when the bag is closed with the zipper as shown in FIGS. 5 and 6. Although door 30 of lock 20 is shown with hinges 32, the door of an alternative embodiment of the lock could have a sliding door that moves out when engaged to block movement of a zipper preventing opening of the bag and moves back when disengaged to allow movement of the zipper and opening of the bag. In one embodiment of the invention, the lock and the bag opener (or means for opening and closing the bag) can be one, such that the lock is, or also contains, the closure mechanism of the bag. In such embodiment, when the lock is engaged, the bag is firmly closed, and when the lock is opened, the bag also opens, as for example with a spring lock mechanism that releases and causes the opening when the lock is opened or released.

The lock itself is an electromechanical type of lock built into or otherwise affixed to the bag so that it cannot easily be removed without noticeably damaging the bag. For example, the lock can be glued or sonic melted to the bag, or can be snapped into place with fittings molded into the bag. In one sense, the lock effectively acts like a "seal" for the bag. While the bag of the invention may not be comprised of an impenetrable material or an unbreakable structure, the bag, for use as a food delivery bag, can maintain the integrity of its contents and will readily reveal tampering if such integrity is compromised, such as by simply tearing into the material comprising the bag. The lock itself is openable only with the unique code for the particular delivery, and that code is available only to the orderer/intended recipient of the food and the restaurant or other food supplier who originally set the code.

Figure 9:
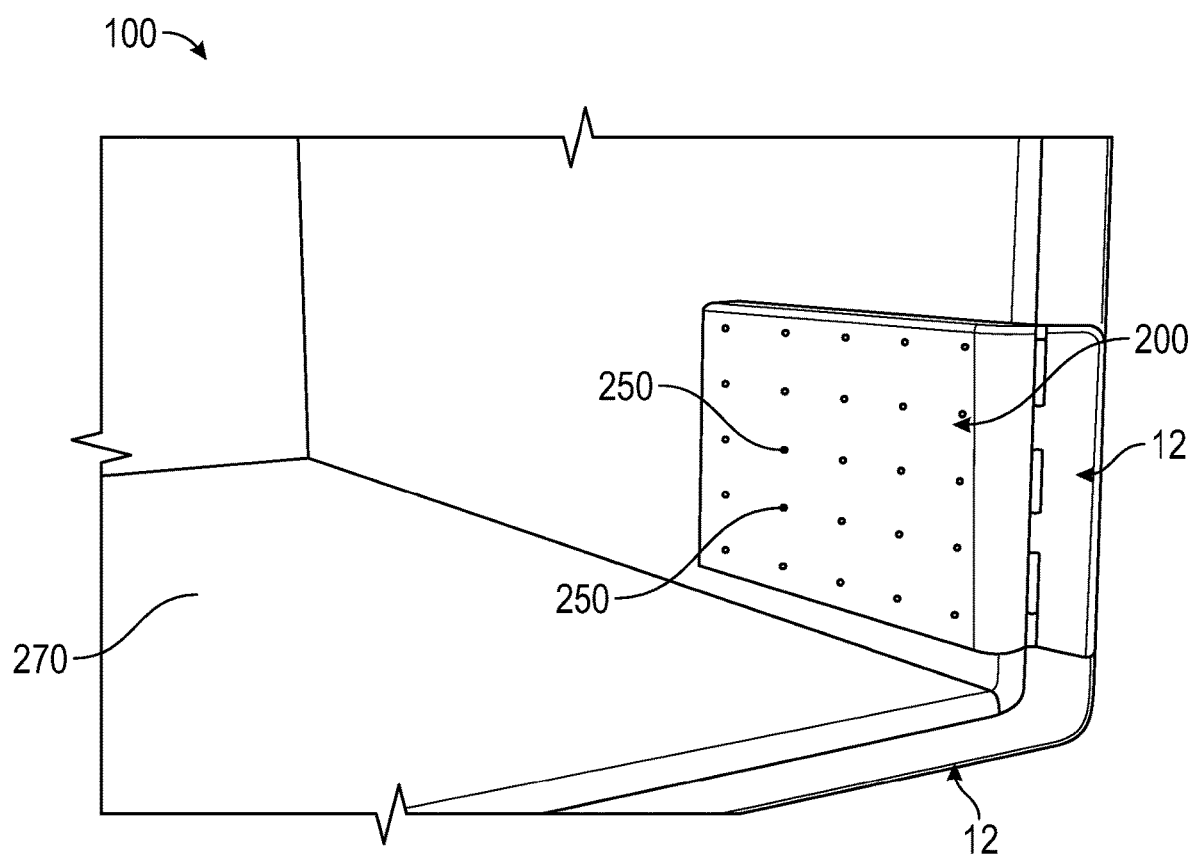
FIG. 9 is a back view of a lock of the invention such as shown in FIG. 7, as the lock is in positioned in place in a bag such as shown in FIGS. 1 and 3, indicating LED lights, such as for example ultraviolet lights, on the back of the lock, which can project light into the interior of the bag.

FIG. 9 illustrates a sanitizing feature of the invention where the lock of the invention further comprises at or on the back of the lock, where the lock is installed in the bag, ultraviolet LED lights which project into the interior space of the bag, particularly the interior space of the bag (such as space 17 in FIG. 1) that will contain the food for and during delivery. Such lights preferably are activated or turned on when the lock is engaged and remain in operation until the lock is opened. In an alternative embodiment, such lights go on and off for a set amount of time each while the lock is engaged. While the LED lights shown are ultraviolet lights to provide sanitation to the bags, i.e., to kill germs with the ultraviolet lights, the LED lights additionally or alternatively could be simply to provide illumination to the interior of the bag and could be white or yellow (or any other color) of LED lights.

The lock of the invention, as noted in the embodiments for example discussed above, can be opened and secured with a QR code or a pin code. That is, the lock provides a temporary QR code or pin code password type of access control where the code is entered on the screen or keyboard (120) of the lock (100). Locks of this type that can be adapted for use in the invention are known and are commercially available. In one embodiment of the invention, the lock can provide both a temporary QR code and a pin code password so that either can be used. Electrical power for operation of the lock can be provided by a battery 240 (shown in FIG. 8), which in one embodiment is rechargeable and can be charged through port 135 (shown in FIG. 7). In one embodiment, such charging can be done in an automobile through auto battery outlets commonly used for cigarette lighters and cell phone charging. Such battery can also charge LED lights or an LED board 250 as shown in FIG. 8.

The features of the lock of the invention, or used in the invention, in various embodiments as discussed in the examples above can be implemented with the help of computer program code that resides in a memory and causes the relevant apparatuses to carry out the method. Generally, and broadly, for example, a tag, a chip or a reader device may comprise circuitry and electronics for handling, receiving and transmitting data, computer program code in a memory, and a processor that, when running the computer program code, causes the reader device to carry out the features of an embodiment. Alternatively or in addition, a tag or a chip for a tag or a reader device may comprise logic circuitry for implementing the same functionality as may be carried out by means of program code run on a processor.

Yet further, a network device may comprise circuitry and electronics for handling, receiving and transmitting data, computer program code in a memory, and a processor that, when running the computer program code, causes the network device to carry out the features of an embodiment. A system may comprise any number of tags of the same kind or different kinds, and reader devices and network computers in any combination.

Figure 10:
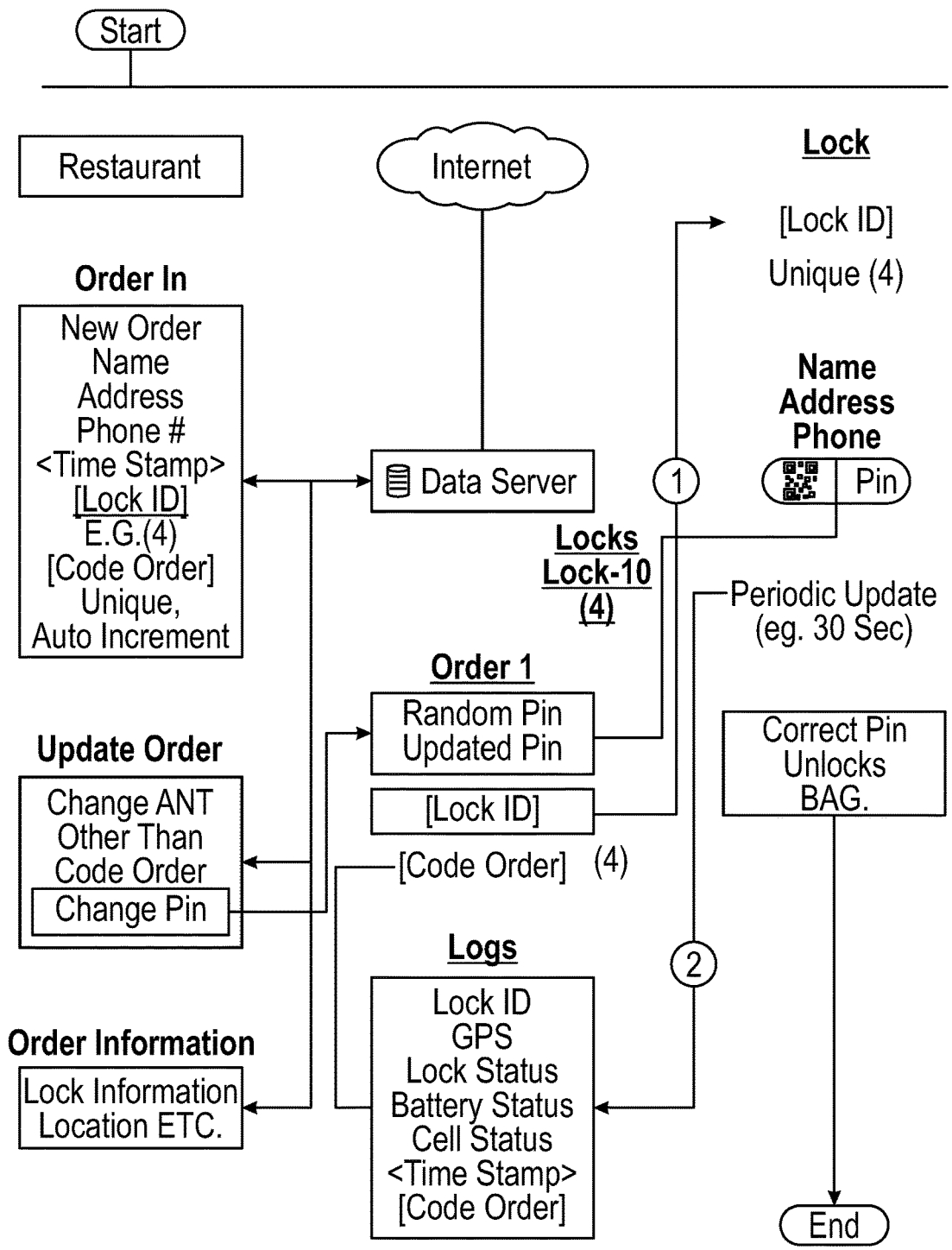
FIG. 10 is a flow chart of the operation of the secure delivery of food from a food provider to a food orderer/consumer using or according to the present invention.

More specifically, FIG. 10 provides a flow chart of the method of using the secure delivery bag of the invention, a method which contributes to the secureness of the delivery of the food contents in the bag. According to the method, the source of the food to be delivered, such as a restaurant, grocery store, or food shop, for example, inserts food in the bag, closes the bag, and engages the lock over the point of opening of the bag so as to prevent the bag from opening until the lock is disengaged. The lock is controlled with a QR code or pin code, which the restaurant, grocery store, or food shop, for example, assigns to the lock for that particular delivery.

A different QR code or pin code is generated for the lock for each use of the lock, and thus for each delivery with the bag. The codes should thus be readily changeable so each delivery with a bag has a unique code for security. Once a QR code or pin code is generated and input in the lock, the QR code or pin code is sent to the orderer and/or intended recipient of the food, preferably via cellular data or the internet, although any transmission through the Internet of Things (IoT) could be used. The food is then physically delivered to that orderer and/or intended recipient of the food, who then opens the bag using the QR code or pin code unique for that delivery. Only such orderer/intended recipient and the restaurant will have the code. The person delivering the food, that is, providing the actual delivery service, will not know the code and will not be able to open the lock.

The Figures and the various embodiments used to describe the principles of the present disclosure in this patent document are by way of illustration only and should not be construed in any way to limit the scope of the disclosure. Further, while preferred embodiments of the present disclosure have been described, it should be understood that other various changes, adaptations, and modifications can be made therein without departing from the spirit of the invention(s).

The invention claimed is:

1. A reusable, secure food delivery bag for securely delivering food from a food supplier to an intended food recipient, comprising:
    a bag;
    a means for closure of the bag, and essentially a single point or location for securing a closure;
    an electromechanical lock with associated, changeable, data code enabled access control; and
    an access keypad or screen;
    wherein said lock fastens over a single point for securing said closure when said lock is activated or closed in position;
    wherein said lock releases and allows access to said closure for opening said bag when said lock is deactivated or opened;
    wherein the data code controlling the deactivation of the lock is sent to the intended food recipient via an internet or cellular data, or through an internet of things;
    wherein entering the data code into said access keypad or displaying the data code to said screen deactivates the lock;

wherein after said lock is deactivated, said data code is changed for reuse of the bag;

and wherein said data code is temporary and uniquely set for each use of the bag.

2. The secure food delivery bag of claim 1 wherein said bag has a frame or structure providing a box-shaped configuration with six sides or a top, bottom and four sides.

3. The secure food delivery bag of claim 1 wherein said data code is a QR code.

4. The secure food delivery bag of claim 1 wherein said data code is a pin code.

5. The secure food delivery bag of claim 1 wherein said electromechanical lock is associated with both a QR code and a pin code.

6. The secure food delivery bag of claim 1 wherein said bag is comprised of hard sided plastic or metal or soft sided plastic or other synthetic polymeric material that is resistant to water and tearing.

7. The secure food delivery bag of claim 1 wherein said means for closure of said bag is a zipper.

8. The secure food delivery bag of claim 1 wherein said means for closure of said bag is effected with two or more zippers where each said zipper opens from the same point or location for securing said bag so that said lock can secure the closure of each said zipper simultaneously when said lock is activated or closed in position.

9. A secure food delivery bag comprising:
   a bag;
   a means for closure of the bag, and essentially a single point or location for securing a closure;
   an electromechanical lock with associated QR code or pin code enabled access control; and
   an access keypad or screen;
   wherein said lock fastens over said single point for securing said closure when said lock is activated or closed in position;
   wherein said lock releases and allows access to said closure for opening said bag when said lock is deactivated or opened;
   wherein the activation and deactivation of said lock is controlled by entering the QR code or pin code associated with said lock into said access keypad or screen;
   wherein said QR code or pin code is temporary and uniquely set for each use of the bag; and
   wherein said bag further comprises LED lights.

10. The secure food delivery bag of claim 9 wherein said LED lights are ultraviolet lights.

11. The secure food delivery bag of claim 10 wherein the ultraviolet lights are positioned in the back of the lock and are activated so as to shine ultraviolet sanitizing light into the interior of the bag when the lock is closed.

12. The secure food delivery bag of claim 9 wherein said means for closure of said bag is a zipper.

13. The secure food delivery bag of claim 9 wherein said means for closure of said bag is effected with two or more zippers where each said zipper opens from the same point or location for securing said bag so that said lock can secure the closure of each said zipper simultaneously when said lock is activated or closed in position.

14. A method for secure delivery of take-out food from a restaurant, grocery store, food shop, or other food supplier to an intended recipient, using the secure delivery bag of claim 1, said method comprising the following steps:
   the food supplier receives an order for food from the intended recipient of the order;
   the food supplier places the ordered food in said secure delivery bag, closes the secure delivery bag, and fastens the bag closed with said lock set and activated with a unique data code;
   the unique data code for opening the lock is sent to the intended recipient via cellular data or the internet or otherwise through the internet of things and the intended recipient receives the unique data code;
   the food supplier gives the secure delivery bag containing the food to a deliverer of the food;
   the deliverer of the food delivers the secure delivery bag to the intended recipient;
   the intended recipient opens the secure delivery bag with the unique data code for the secure delivery bag and takes the food from the bag.

15. The method of claim 14 further comprising the following additional steps:
   after removing the food from the bag, the intended recipient returns the secure delivery bag to the deliverer who returns the secure delivery bag to the food supplier; and the data code for the secure delivery bag resets with a different data code, after which the food supplier reuses the secure delivery bag.

16. A reusable, secure, food delivery bag for securely delivering food from a food supplier to an intended food recipient, comprising:
   a bag;
   a means for closure of the bag and also for securing a closure, said means comprising an electromechanical lock openable only with a changeable, unique data code that is set for one-time use for each use of the bag, such that the bag is firmly closed when the lock is engaged or activated and the bag is open when the lock is released or deactivated;
   and an access keypad or screen;
   wherein the unique data code controlling the deactivation of the lock is sent to the intended food recipient via an internet or cellular data, or through an internet of things;
   wherein entering the unique code into said access keypad or displaying the unique data code to said screen deactivates the lock and opens the bag;
   and wherein after said lock is deactivated, said unique data code is changed for reuse of the bag.

17. A method for secure delivery of take-out food from a restaurant, grocery store, food shop, or other food supplier to an intended recipient, using the secure delivery bag of claim 16, said method comprising the following steps;
   the food supplier receives an order for food from the intended recipient of the order;
   the food supplier places the ordered food in said secure delivery bag and engages or activates the lock, closing the bag;
   the unique data code for opening the lock is sent to the intended recipient via cellular data or the internet or otherwise through the internet of things and the intended recipient receives the unique data code;
   the food supplier gives the secure delivery bag containing the food to a deliverer of the food;
   the deliverer of the food delivers the secure delivery bag to the intended recipient;
   the intended recipient opens the secure delivery bag with the unique data code for the secure delivery bag and takes the food from the bag.

18. The method of claim 17 further comprising the following additional steps:

after removing the food from the bag, the intended recipient returns the secure delivery bag to the deliverer for returning the secure delivery bag to the food supplier, and the data code resets for reuse of the secure delivery bag.

\* \* \* \* \*